US010952765B2

(12) United States Patent
Petranto

(10) Patent No.: US 10,952,765 B2
(45) Date of Patent: Mar. 23, 2021

(54) SYSTEMS, DEVICES, AND NON-INVASIVE SURGICAL METHODS FOR TREATING PLANTAR FASCIITIS AND CHRONIC HEEL SPUR SYNDROME

(71) Applicant: Russell D. Petranto, Seaside Park, NJ (US)

(72) Inventor: Russell D. Petranto, Seaside Park, NJ (US)

( * ) Notice: Subject to any disclaimer, the term of this patent is extended or adjusted under 35 U.S.C. 154(b) by 109 days.

(21) Appl. No.: 16/119,789

(22) Filed: Aug. 31, 2018

(65) Prior Publication Data

US 2020/0069326 A1 Mar. 5, 2020

(51) Int. Cl.
*A61B 17/3209* (2006.01)
*A61M 5/32* (2006.01)
*A61B 5/00* (2006.01)

(52) U.S. Cl.
CPC ....... *A61B 17/32093* (2013.01); *A61M 5/329* (2013.01); *A61B 5/0071* (2013.01); *A61M 2210/086* (2013.01)

(58) Field of Classification Search
CPC .......... A61B 5/0071; A61B 17/320036; A61B 17/320016; A61B 17/32093;
(Continued)

(56) References Cited

U.S. PATENT DOCUMENTS 5,253,659 A 10/1993 McNamara et al.
5,269,290 A * 12/1993 Barrett ........... A61B 17/320036
128/898

(Continued)

OTHER PUBLICATIONS

OrthoFlo, www.mimedx.com/orthoflo, MiMedX Group, Inc., Marietta, Georgia, Aug. 31, 2018, 3 pages.
(Continued)

*Primary Examiner* — Lauren P Farrar
*Assistant Examiner* — Hamza A Darb
(74) *Attorney, Agent, or Firm* — Doherty IP Law Group LLC

(57) ABSTRACT

A method of treating plantar fasciitis or chronic heel spur syndrome includes inserting a first needle having a distal tip into a plantar aspect of a foot and advancing the distal tip to a location where a plantar fascia originates, and inserting a second needle having a distal tip into a medial aspect of the foot and advancing the distal tip of the second needle to the location where the plantar fascia originates. Medical imaging confirms that the distal tips of the first and second needles are located where the plantar fascia originates. After medical imaging, the second needle is removed from the foot, and a third needle having a sharpened distal tip is inserted into a medial opening formed by the second needle. The sharpened distal tip of the third needle is advanced through the medial opening to the location where the plantar fascia originates. Medical imaging confirms the location of the sharpened distal tip of the third needle. The sharpened distal tip of the third needle is used to cut the plantar fascia. After cutting the plantar fascia, the third needle is removed from the foot. A fourth needle coupled with a syringe containing a growth factor is inserted into the medial opening in the foot, and a distal tip of the fourth needle is advanced to the location where the plantar fascia originates. Medical imaging confirms the location of the distal tip of the fourth needle. The syringe coupled with the fourth needle is engaged for injecting the growth factor into the plantar fascia.

20 Claims, 20 Drawing Sheets

(58) Field of Classification Search
CPC . A61B 17/3403; A61B 5/6849; A61B 5/6848; A61M 5/329; A61M 2210/086; A61M 5/34; A61M 60/34
See application file for complete search history.

(56) References Cited

U.S. PATENT DOCUMENTS

| | | | |
|---|---|---|---|
| 2009/0203975 A1* | 8/2009 | Barrett | A61B 17/3417 600/306 |
| 2010/0247513 A1* | 9/2010 | Agee | A61K 31/56 424/94.67 |
| 2014/0107553 A1 | 4/2014 | Bushby | |
| 2015/0366576 A1* | 12/2015 | Liou | A61B 17/320016 606/170 |
| 2017/0042565 A1* | 2/2017 | Ellsworth | A61B 17/320016 |

OTHER PUBLICATIONS

BioD at a Glance, www.biodlogics.com/about-us/corporate-infirmation, Integra Lifesciences Corporation, Plainsboro, New Jersey, Aug. 31, 2018, 2 pages.

* cited by examiner

SYSTEMS, DEVICES, AND NON-INVASIVE SURGICAL METHODS FOR TREATING PLANTAR FASCIITIS AND CHRONIC HEEL SPUR SYNDROME

BACKGROUND OF THE INVENTION

Field of the Invention

The present patent application is generally related to surgical procedures, and is more specifically related to systems, devices and methods of treating chronic foot pain and plantar fasciitis.

Description of the Related Art

FIG. 1 shows a dissected view of the bottom of a human foot 50 including a heel region 52 having a heel bone 54 and a ball region 56 adjacent toes 58A-58E. The foot includes a plantar fascia 60 that extends across the bottom of the foot 50 from the heel region 52 to the ball region 56. The plantar fascia 60 serves a vital role of maintaining the shape of the two anatomical arches of the foot, the transverse arch and the longitudinal arch. The plantar fascia 60 has different parts including a medial plantar fascia 62, superficial tracks 64, a central component 66, and a lateral component 68. When an individual walks, the separate parts of the plantar fascia 60 work together to function as a shock absorber and to transfer tension forces over the bottom of the foot 50.

Referring to FIGS. 2A and 2B, the plantar fascia 60 is thick and essentially inelastic. Overstressing the plantar fascia 60 may produce tears in the plantar fascia or separate the plantar fascia from the heel bone 54 and other surrounding tissues of the foot 50. Tearing and separation of the plantar fascia 60 produces painful inflammation commonly referred to as plantar fasciitis. In FIGS. 2A and 2B, the inflamed area 70 of the plantar fascia 60 is located near the heel bone 54 in the heel region 52 of the foot 50. In other instances, the pain from plantar fascia may be felt along the arch region of the foot 50.

Left untreated, plantar fasciitis may become very debilitating so that common activities such as walking and standing are very painful. Common non-surgical treatments for plantar fasciitis may include stretching the plantar fascia, bed rest, applying ice packs to the bottom of the feet, using night splints and wedge-shaped arch supports, ingesting oral anti-inflammatories, and receiving steroid injections. Non-surgical treatments have not proven to be very successful.

In some instances, treating chronic, severe cases of plantar fasciitis may require corrective surgery on the plantar fascia. For example, U.S. Pat. No. 5,253,659 discloses an endoscopic system and method for performing endoscopic surgery at locations where tissue inserts into bone. The system has a sleeve member, an obturator, cutting and excision instruments, and a marking and insertion assembly. The sleeve member has an expanded portal through which instrument access and improved visualization can be performed at arcuate lines of insertion of tissue into bone. The sleeve member has a flange for engaging tissue along the line of insertion and exposing the bone and measurement means for gauging precisely the reduction or resection of bone. Cutting instruments are provided with an extension portion to extravasate from tissue and palpitate underlying tissue. A marking and insertion assembly for use in heel surgeries to remedy plantar fasciitis and in conjunction with a lateral radiograph provides precise location of an entry incision and precise medial to lateral insertion of a guide wire forming a channel for the sleeve member. The method and system also provides for minimal incision surgery in the caudal release of the plantar fascia and reduction of a spur.

Despite achieving some success when using surgical methods, operative intervention is generally more costly and includes a higher risk of complication than nonsurgical treatments for the patient.

Thus, there remains a continuing need for non-invasive surgical methods, systems and devices for treating chronic heel pain and plantar fascia.

SUMMARY OF THE INVENTION

In one embodiment, a surgical procedure is utilized to treat patients suffering from chronic heel pain and plantar fasciitis. In one embodiment, the surgical procedure includes performing a plantar fasciotomy in conjunction with injecting a growth factor at the location where the plantar fascia is cut. In one embodiment, fluoroscopy is utilized for guiding the instruments utilized for cutting the plantar fascia and injecting the growth factor.

In one embodiment, a surgeon preferably utilizes local anesthesia on a patient's foot to treat plantar fascia. In one embodiment, a 25 gauge needle or similarly sized needle is placed along the plantar surface of the patient's foot, directed at the origination of the plantar fascia at the plantar aspect of the calcaneus at the level of the spur formation. Next, a second needle is placed at the medial aspect of the calcareous directed at the origination of the plantar fascia. The location of the two needles that have been positioned is confirmed using fluoroscopy. Next, the medial guided needle is removed followed by insertion of a larger needle, such as an 18 gauge needle. The position of the larger needle is confirmed at its location at the origination of the medial band of the plantar fascia using fluoroscopy. After the 18 gauge needle has been inserted, light strokes starting from the medial origination of the plantar fascia are performed moving from a medial direction to a lateral direction across the origination of the plantar fascia and totaling approximately two-thirds of the medial fascia band of the plantar fascia. The plantar fascia is cut or incised using the sharpened distal tip of the 18 gauge needle.

In one embodiment, after the plantar fascia has been cut, the 18 gauge needle is removed and a smaller sized needle such as a 22 gauge needle is inserted into the medial needle guided entrance point and directed toward the location where the plantar fascia has been cut. The location of the 22 gauge needle is confirmed using fluoroscopy. Next, a growth factor, such as a stem cell derived growth factors, is injected into the location where the plantar fascia has been cut, through the bore of the 22 gauge needle at the level of the medial band plantar fasciotomy. Growth factors may include naturally occurring substances capable of stimulating cellular growth, proliferation, healing, and cell differentiation.

In one embodiment, the growth factor may be derived from either human or porcine cellular allografts. In one embodiment, the growth factor is a regenerative and/or therapeutic biologic that is preferably derived from stem cells. In one embodiment, the stem cells may be obtained from amniotic fluid, a placenta, an umbilical cord, an amniotic membrane, chorion, or combinations thereof, from either human cellular allografts or porcine cellular allografts. In one embodiment, the growth factor desirably promotes healing and minimizes inflammation. In one embodiment, the growth factors may be an injectable human amniotic fluid allograft sold under the trademark ORTHO-FLOW™ by MiMedX Group, Inc. of Marietta, Ga. In one embodiment, the growth factors may be biologic products derived from the placental tissues sold under the trademark BioD™ by Integra Lifesciences Corporation of Plainsboro, N.J.

In one embodiment, the smaller bore needle, such as a 22 gauge needle, is removed and an adhesive bandage is applied over the medial entrance. In one embodiment, the first 25 gauge needle is removed from the plantar region and an adhesive bandage is applied over the plantar entrance.

In one embodiment, a method of treating plantar fasciitis preferably includes inserting a first needle having a distal tip into a plantar aspect of a foot and advancing the distal tip of the first needle to a location where a plantar fascia originates. In one embodiment, the method desirably includes inserting a second needle having a distal tip into a medial aspect of the foot and advancing the distal tip of the second needle to the location where the plantar fascia originates. In one embodiment, advancing the distal tip of the second needle into the medial aspect forms a medial opening in the foot.

In one embodiment, medical imaging is used to confirm that the distal tips of the first and second needles are located where the plantar fascia originates.

In one embodiment, after the medical imaging step, the second needle is removed from the foot, and a third needle having a sharpened distal tip is inserted into the medial opening in the foot. In one embodiment, the sharpened distal tip of the third needle is advanced to the location where the plantar fascia originates.

In one embodiment, medical imaging is used to confirm that the sharpened distal tip of the third needle is located where the plantar fascia originates.

In one embodiment, the sharpened distal tip of the third needle is used for cutting the plantar fascia. After the plantar fascia is cut, the third needle may be removed from the foot, and a fourth needle, coupled with a syringe containing a growth factor, has a distal tip that is preferably inserted into the medial opening in the foot. In one embodiment, the distal tip of the fourth needle is advanced to the location where the plantar fascia originates.

In one embodiment, after the fourth needle is inserted, medical imaging confirms that the distal tip of the fourth needle is located where the plantar fascia originates. In one embodiment, the syringe coupled with the fourth needle is engaged for injecting the growth factor into the plantar fascia.

In one embodiment, the third needle has a larger outer diameter than both the second needle and the fourth needle. In one embodiment, the first and second needles have an identical outer diameter. In one embodiment, the first and second needles are 25 gauge needles, the third needle is an 18 gauge needle, and the fourth needle is a 22 gauge needle.

In one embodiment, the medical imaging process uses a fluoroscope.

In one embodiment, the cutting step preferably includes moving the sharpened distal tip from a medial direction to a lateral direction across the plantar fascia at the location where the plantar fascia originates.

In one embodiment, after injecting the growth factor, the first and fourth needles are removed from the foot, and bandages are placed over the wounds formed by the first and fourth needles.

In one embodiment, a method of treating plantar fasciitis preferably includes inserting a first 25 gauge needle having a distal tip into a plantar aspect of a foot and advancing the distal tip of the first 25 gauge needle to a location where a plantar fascia originates, and inserting a second 25 gauge needle having a distal tip into a medial aspect of the foot and advancing the distal tip of the second 25 gauge needle to the location where the plantar fascia originates, whereby the advancing the distal tip of the second 25 gauge needle step forms a medial opening in the foot.

In one embodiment, a fluoroscope is used for confirming that the distal tips of the first and second 25 gauge needles are located where the plantar fascia originates. In one embodiment, after using the fluoroscope, the second 25 gauge needle is removed from the foot, and an 18 gauge needle having a sharpened distal tip is inserted into the medial opening in the foot. In one embodiment, the sharpened distal tip of the 18 gauge needle is advanced to the location where the plantar fascia originates.

In one embodiment, a fluoroscope is used for confirming that the sharpened distal tip of the 18 gauge needle is located where the plantar fascia originates. In one embodiment, the sharpened distal tip of the 18 gauge needle is used for cutting the plantar fascia.

In one embodiment, after the plantar fascia is cut, the 18 gauge needle is preferably removed from the foot.

In one embodiment, a 22 gauge needle coupled with a syringe containing a growth factor is utilized. In one embodiment, a distal tip of the 22 gauge needle is inserted into the medial opening in the foot. In one embodiment, the distal tip of the 22 gauge needle is advanced to the location where the plantar fascia originates. A fluoroscope may be used for confirming that the distal tip of the 22 gauge needle is located where the plantar fascia originates. The syringe coupled with the 22 gauge needle may be engaged for injecting the growth factor into the plantar fascia.

In one embodiment, the cutting step may include moving the sharpened distal tip of the 18 gauge needle from a medial direction to a lateral direction across the plantar fascia at the location where the plantar fascia originates.

In one embodiment, after the growth factor is injected, the first 25 gauge needle and the 22 gauge needle may be removed from the foot. Bandages may be placed over the wounds formed by the first 25 gauge needle and the 22 gauge needle.

In one embodiment, a method of treating plantar fasciitis desirably includes inserting a first needle having a distal tip into a plantar aspect of a foot and advancing the distal tip of the first needle to a location where a plantar fascia originates, and inserting a second needle having a distal tip into a medial aspect of the foot and advancing the distal tip of the second needle to the location where the plantar fascia originates, thereby forming a medial opening in the foot.

In one embodiment, fluoroscopy is used for confirming that the distal tips of the first and second needles are located where the plantar fascia originates. In one embodiment, after the fluoroscopy step, the second needle is removed from the foot, and a third needle having a sharpened distal tip is inserted into the medial opening in the foot, and advancing the sharpened distal tip of the third needle to the location where the plantar fascia originates.

In one embodiment, fluoroscopy is used for confirming that the sharpened distal tip of the third needle is located where the plantar fascia originates.

In one embodiment, the sharpened distal tip of the third needle is used for cutting the plantar fascia. After the cutting the plantar fascia step, the third needle is preferably removed from the foot.

In one embodiment, a fourth needle is provided and coupled with a syringe containing growth factors. In one embodiment, a distal tip of the fourth needle is inserted into the medial opening in the foot, and the distal tip of the fourth needle is advanced to the location where the plantar fascia originates.

In one embodiment, fluoroscopy is used for confirming that the distal tip of the fourth needle is located where the plantar fascia originates, and the syringe coupled with the fourth needle may be engaged for injecting the growth factor into the plantar fascia.

In one embodiment, the sharpened distal tip of the third needle preferably includes at least one cutting edge.

In one embodiment, the third needle is coupled with a syringe prior to the cutting the plantar fascia step.

In one embodiment, the cutting the plantar fascia step preferably includes moving the sharpened distal tip of the third needle from a medial direction to a lateral direction across the plantar fascia at the location where the plantar fascia originates. In one embodiment, the cutting the plantar fascia step include moving the sharpened distal tip of the third needle in dorsal and plantar directions. In one embodiment, the sharpened distal tip may be repeatedly swung back and forth in an arc having a range of about 30-45 degrees (dorsal to plantar) for cutting the plantar fascia.

These and other preferred embodiments of the present invention will be described in more detail below.

DETAILED DESCRIPTION OF PREFERRED EMBODIMENTS

Figure 1:
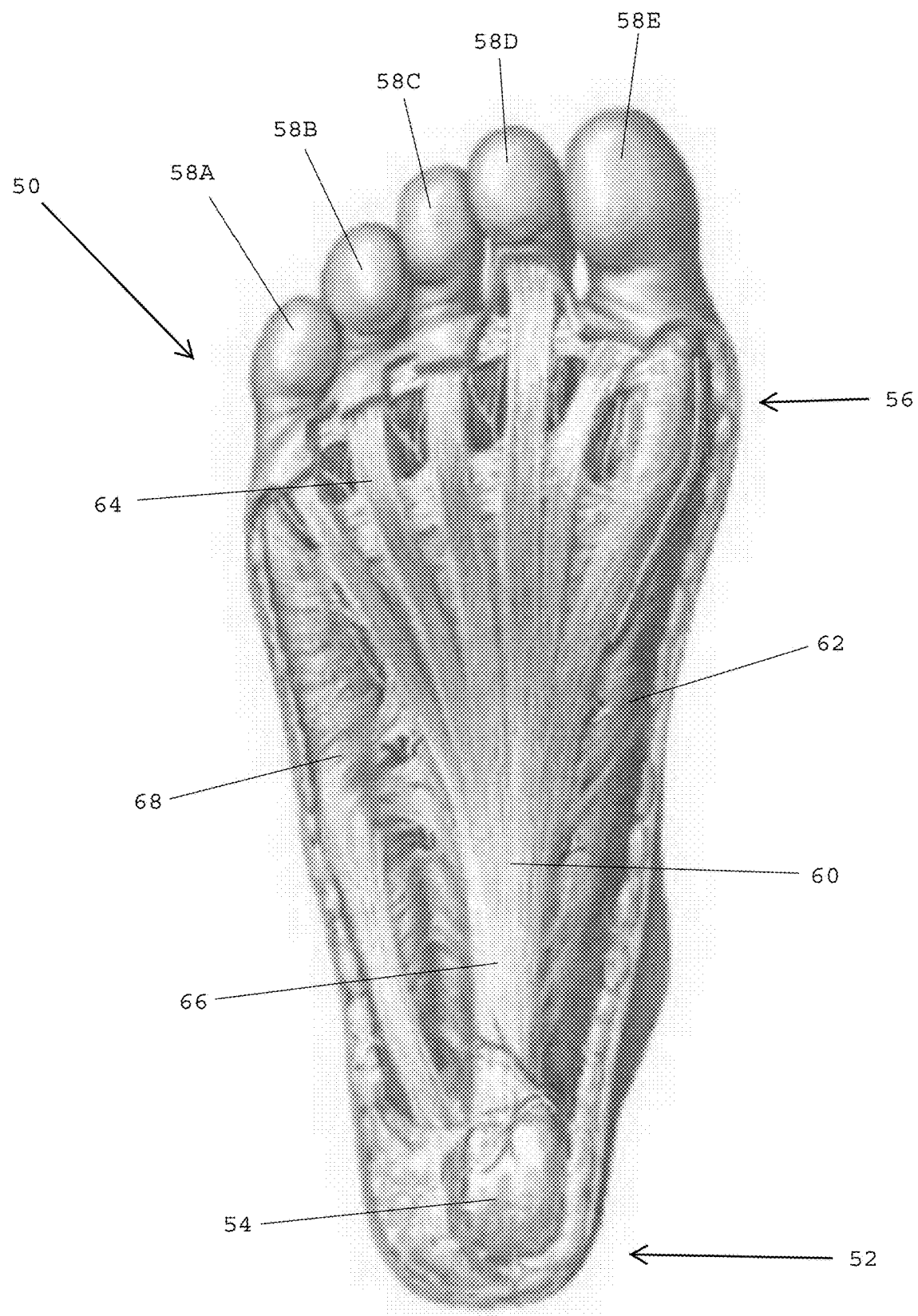
FIG. 1 shows a bottom view of a dissected foot having a plantar fascia that extends between the heel region and the ball region of the foot.
Figure 2A:
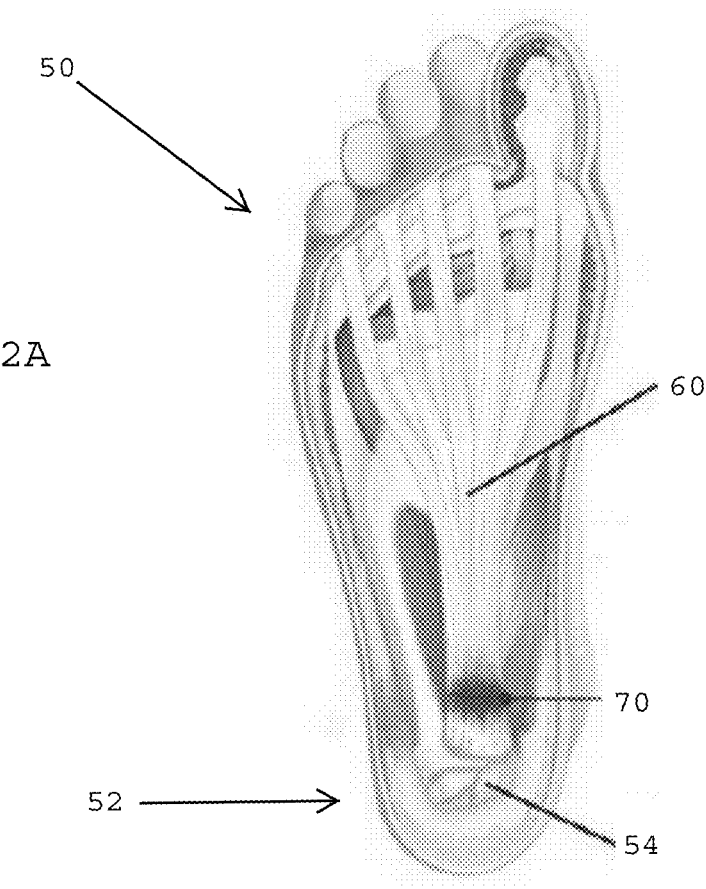
FIG. 2A shows a bottom view of a foot having an inflamed plantar fascia.
Figure 2B:
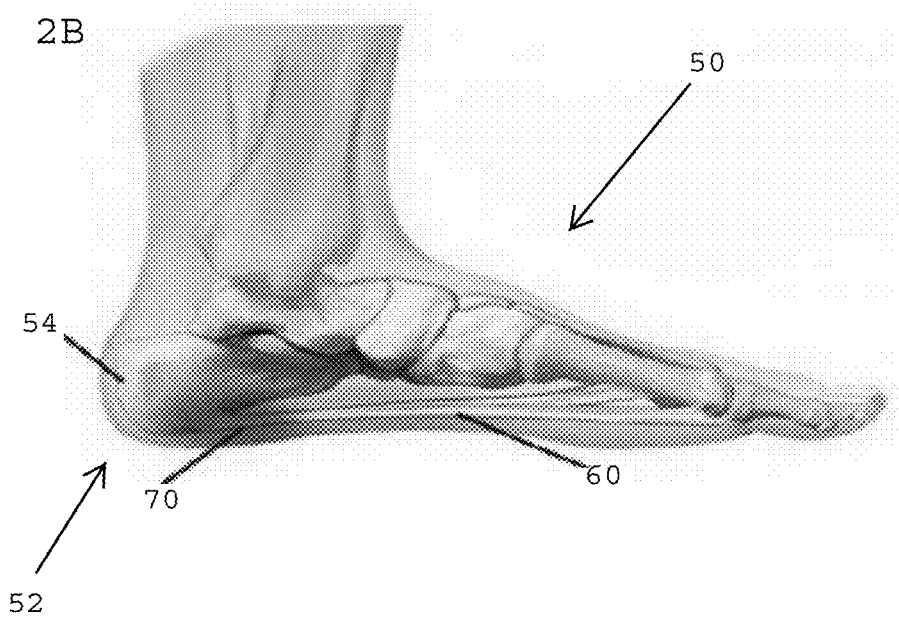
FIG. 2B shows a cross-sectional side view of the foot shown in FIG. 2A having the inflamed plantar fascia.
Figure 3:
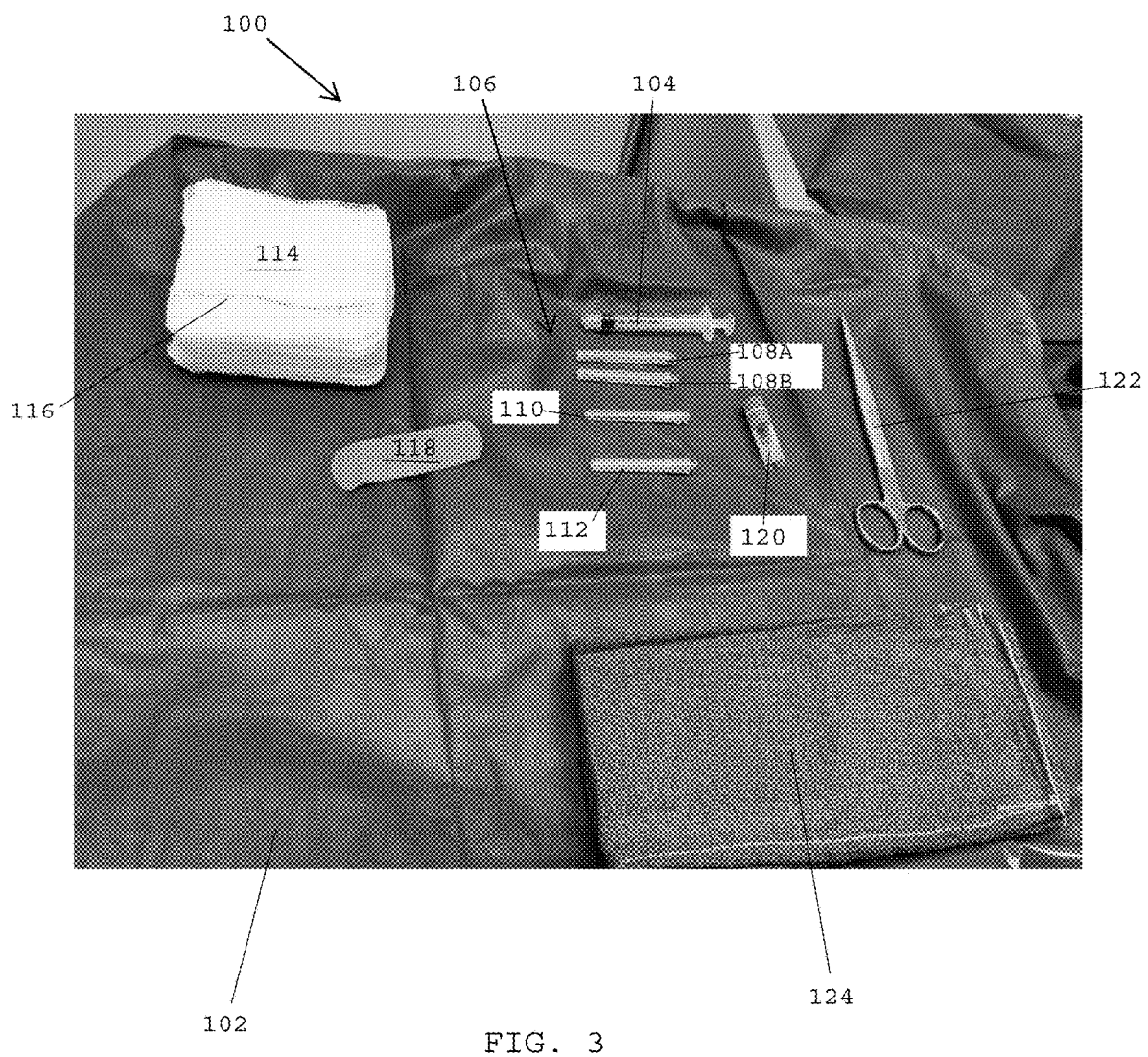
FIG. 3 shows a perspective view of a surgical kit utilized for performing a surgical procedure on patients suffering from chronic heel pain and plantar fasciitis, in accordance with one embodiment of the present patent application.

Referring to FIG. 3, in one embodiment, a surgical kit 100 for performing a plantar fasciotomy procedure preferably includes various tools positioned atop a surgical tarp 102, which, in turn, may be positioned over a table such as a Mayo stand. In one embodiment, the surgical kit 100 desirably includes at least one syringe 104 and a plurality of needles 106 having various sizes or gauges. In one embodiment, the needles 106 are adapted to be coupled with a distal end of the at least one syringe 104. In one embodiment, the syringe 104 is preferably a 2-10 cc syringe and more preferably about a 3 cc syringe. In one embodiment, the needles 106 may include 25 gauge needles 108A, 108B, an 18 gauge needle 110, and a 22 gauge needle 112.

In one embodiment, the surgical kit 100 preferably includes a plurality of surgical sponges 114, such as Raytek sponges having a radio opaque strip 116, and adhesive bandages 118 having gauze pads in the center, which are adapted to be placed over minor wounds and/or surgical openings created by the needles 106.

In one embodiment, the surgical kit 100 preferably includes a vial or container of a human growth factor 120 that may be injected into a patient using the syringe 104 and one of the needles 106. The surgical kit 100 may include scissors 122, and sterile surgical drapes 124 that may be positioned over a patient's foot. The surgical kit 100 shown in FIG. 3 is exemplary in nature only and may be modified by medical personnel depending upon the needs of a patient, a surgeon, and/or the particular plantar fasciitis procedure being performed.

Figure 4:
FIG. 4 shows a stage of a surgical procedure for treating plantar fascia during which a first needle is inserted into the plantar region of a foot, in accordance with one embodiment of the present patent application.

Referring to FIG. 4, in one embodiment, during a first stage of a surgical procedure, a sterile surgical drape 124 is desirably positioned over a patient's foot F. In one embodiment, the sterile surgical drape 124 is positioned over the patient's foot so that the patient's heel region remains accessible to surgical personnel. In one embodiment, a surgeon preferably selects a first 25 gauge needle 108A and inserts the sharpened tip of the first 25 gauge needle 108A into the heel or plantar region of the patient's foot. The sharpened tip is preferably advanced until the tip is positioned at the location where the plantar fascia originates at the heel bone.

Figure 5:
FIG. 5 shows another stage of a surgical procedure for treating plantar fascia during which a second needle is inserted into a medial portion of a foot, in accordance with one embodiment of the present patent application.

Referring to FIG. 5, in one embodiment, after the first 25 gauge needle 108A has been positioned in the plantar region of the foot, the second 25 gauge needle 108B is preferably inserted into the medial region of the foot F. In one embodiment, the tip of the second 25 gauge needle 108B is advanced until the distal tip of the needle is positioned at the location where the plantar fascia originates with the heel bone.

Figure 6:
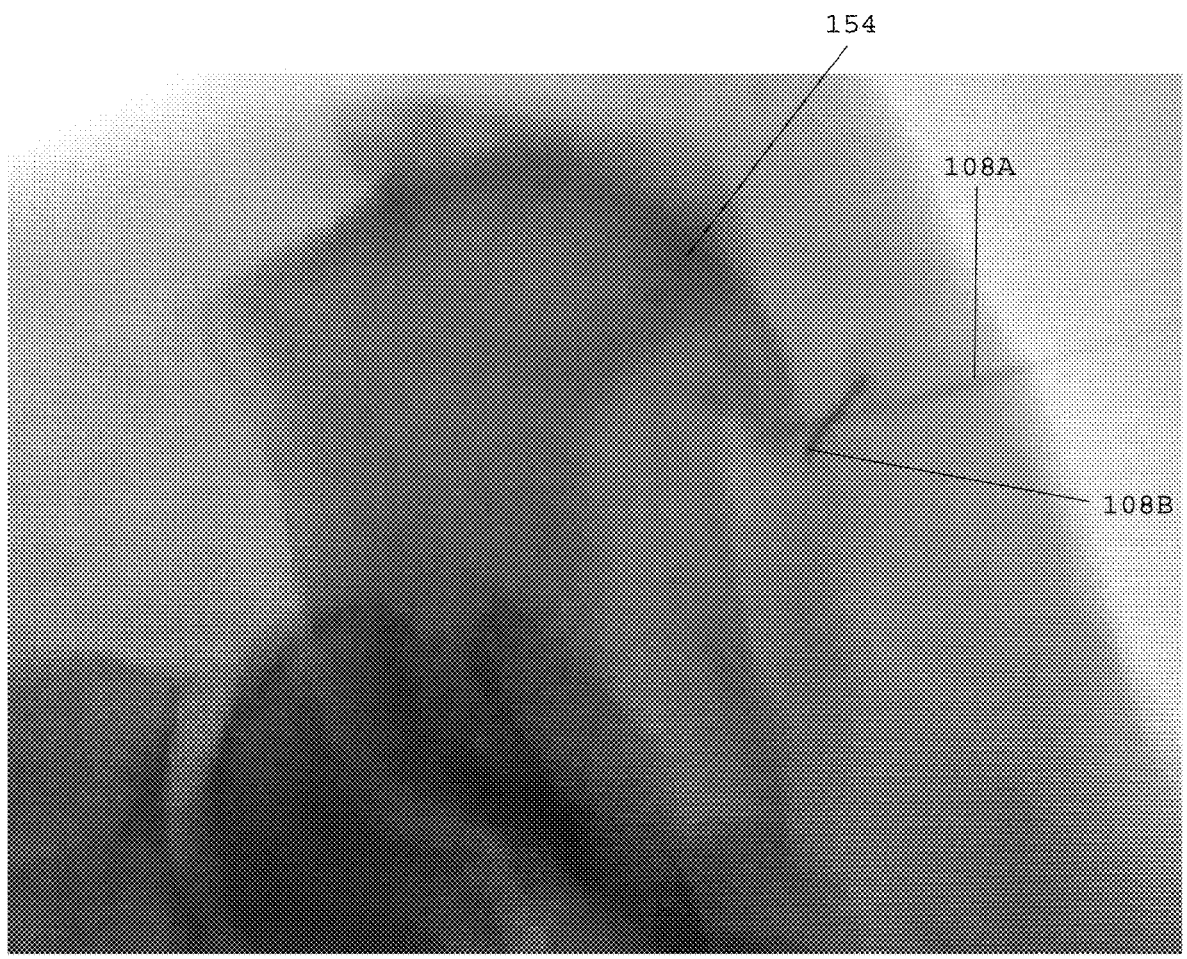
FIG. 6 shows yet another stage of a surgical procedure for treating plantar fascia during which fluoroscopy is utilized to determine the orientation and location of the first and second needles inserted during the stages shown in FIGS. 4 and 5, in accordance with one embodiment of the present patent application.

Referring to FIG. 6, in one embodiment, after the first and second 25 gauge needles 108A, 108B (FIG. 5) have been inserted into the respective plantar and medial regions of the patient's foot, fluoroscopy may be utilized to confirm the exact location of the distal tips of the respective first and second 25 gauge needles 108A, 108B. During the fluoroscopy procedure, surgical personnel preferably confirm that the distal tips of the respective 25 gauge needles 108A, 108B are positioned at the location where the plantar fascia originates. In one embodiment, the plantar fascia originates at the patient's heel bone 154. If the fluoroscopy procedure indicates that the tips of the 25 gauge needles are not properly positioned at the location where the plantar fascia originates, surgical personnel, using fluoroscopic images, may adjust the locations of the respective distal tips of the 25 gauge needles 108A, 108B until the distal tips are properly positioned at the location where the plantar fascia originates.

After it has been determined that the medially placed second 25 gauge needle 108B has been properly positioned in the foot, a surgeon may prepare the 18 gauge needle 110 (FIG. 3) for use in the procedure. In one embodiment, the second 25 gauge needle 108B (FIG. 5) is removed from the medial region of the foot and replaced by the 18 gauge needle 110 (FIG. 3), which is preferably inserted into the opening created by the second 25 gauge needle 108B.

Figure 7A:
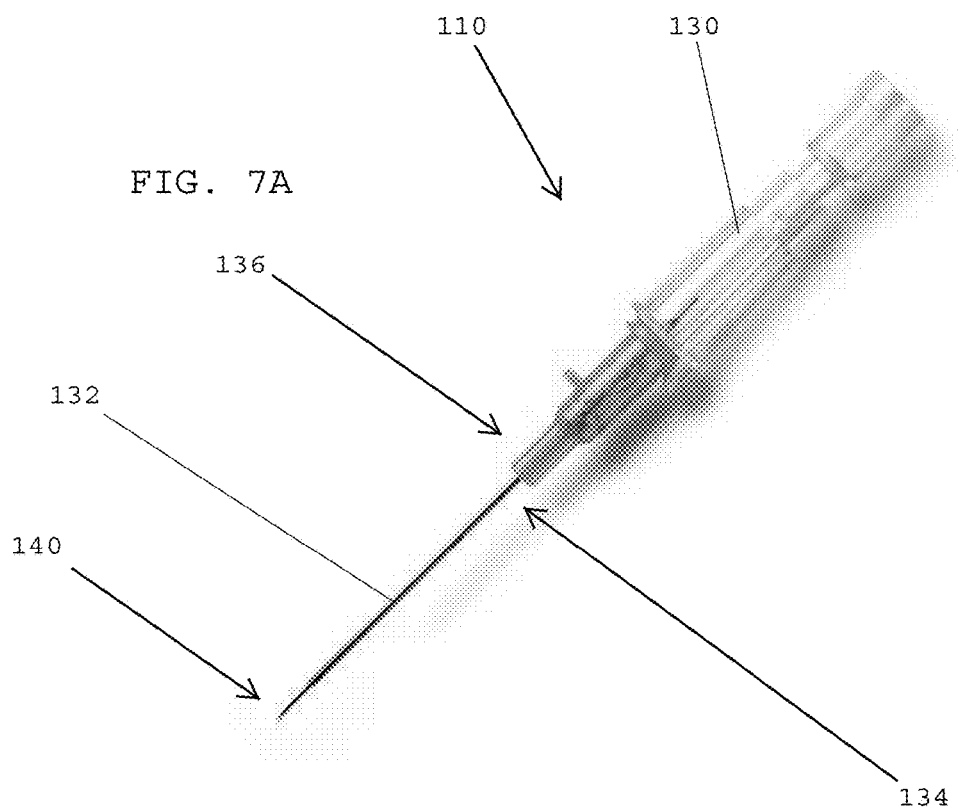
FIG. 7A shows a perspective view of a needle utilized for dissecting a plantar fascia, in accordance with one embodiment of the present patent application.
Figure 7B:
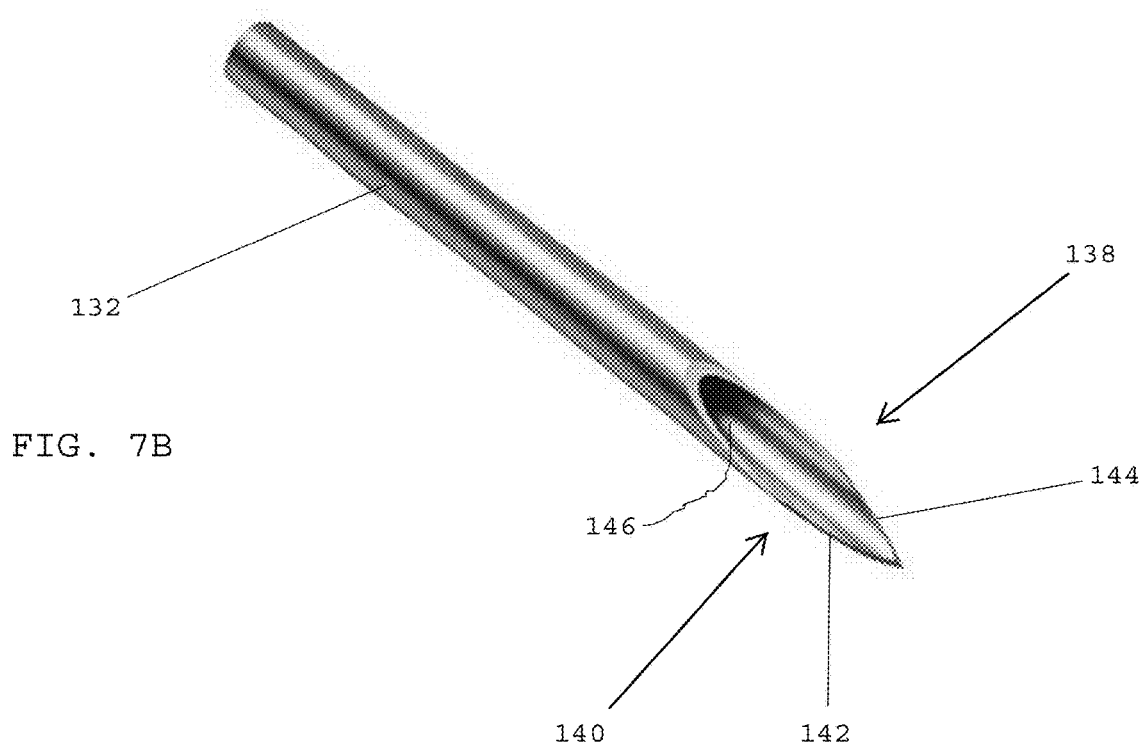
FIG. 7B shows a sharpened distal tip of the needle shown in FIG. 7A.

Referring to FIGS. 7A and 7B, in one embodiment, the 18 gauge needle 110 preferably includes a handle 130 and an elongated shaft 132 having a proximal end 134 secured to a distal end 136 of the handle 130. In one embodiment, the elongated shaft 132 preferably has a distal end 138 including a sharpened tip 140 with cutting edges 142, 144. The elongated shaft 132 preferably defines an elongated conduit 146 that extends along the length of the elongated shaft 132.

Figure 8:
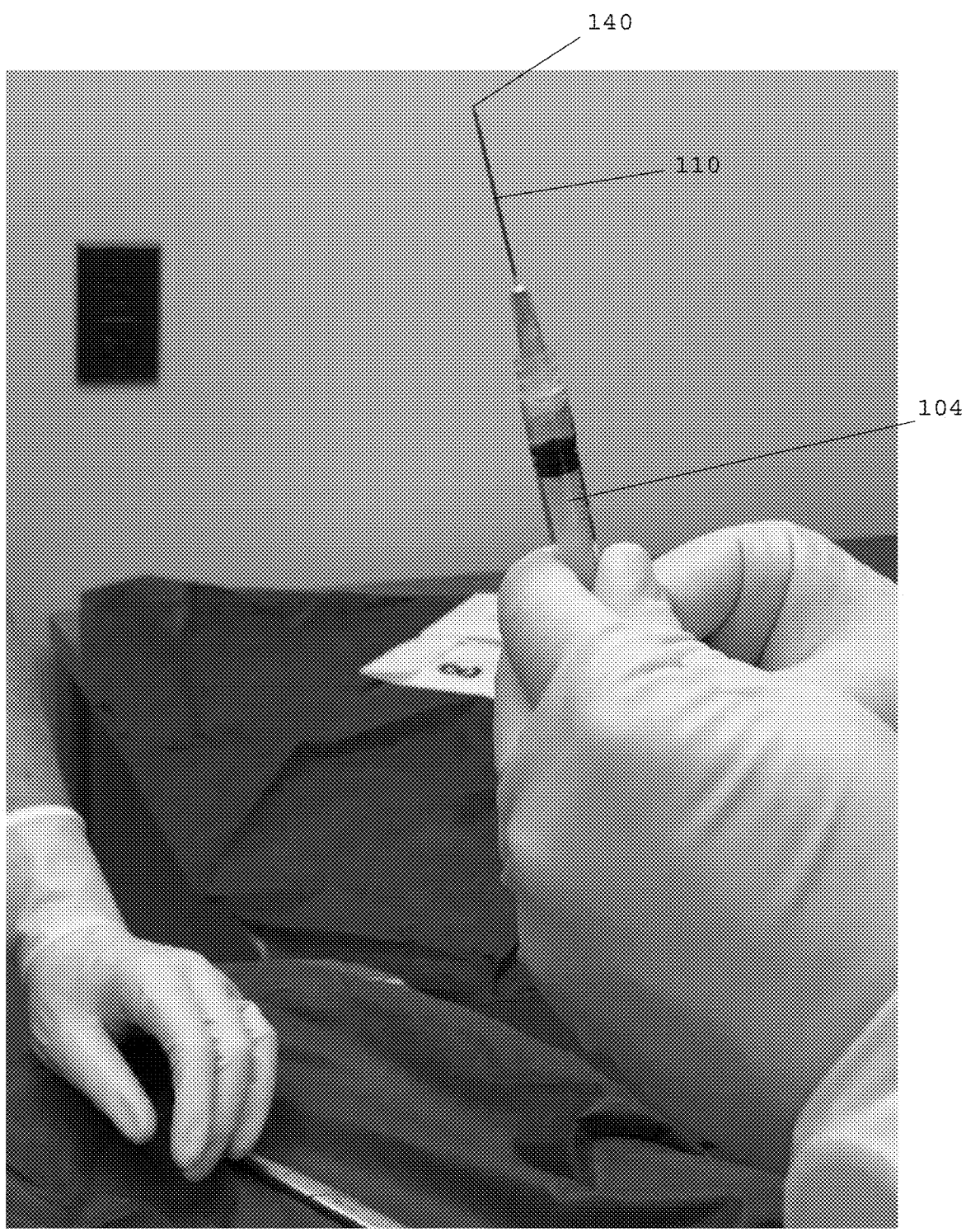
FIG. 8 shows the needle of FIGS. 7A and 7B after it has been coupled with a syringe for use during a plantar fasciitis procedure, in accordance with one embodiment of the present patent application.

Referring to FIG. 8, in one embodiment, the 18 gauge needle 110 may be prepared for use by securing the 18 gauge needle to the distal end of the syringe 104 (FIG. 3).

Figure 9:
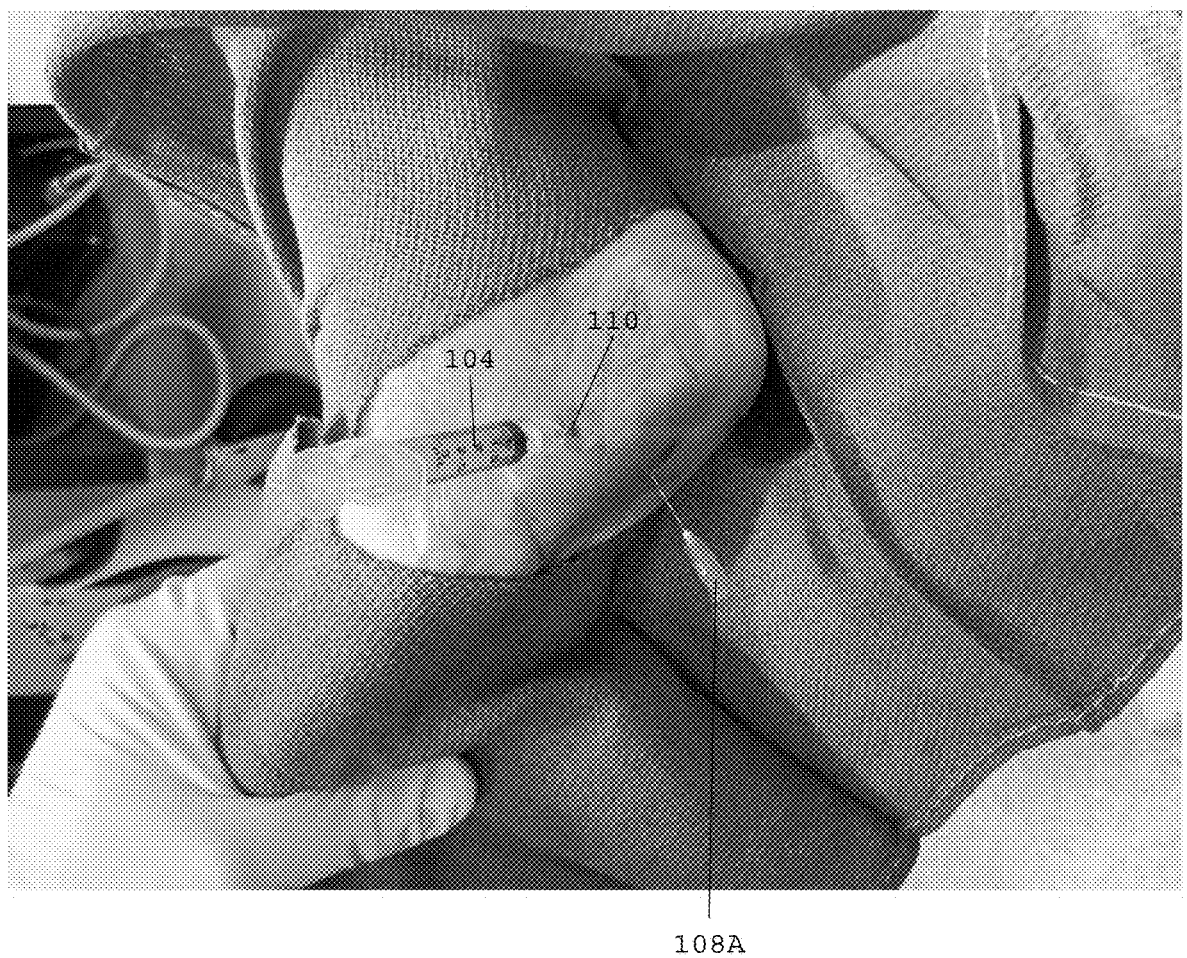
FIG. 9 shows the needle of FIG. 8 being inserted into the medial region of a foot, in accordance with one embodiment of the present patent application.

Referring to FIG. 9, in one embodiment, the second 25 gauge needle 108B (FIG. 5) may be removed from the medial portion of the foot and replaced by the 18 gauge needle 110 that is coupled with the syringe 104. As noted above, the 18 gauge needle 110 is preferably inserted into and advanced through the medial opening previously formed by the second 25 gauge needle 108B (FIG. 5). The first 25 gauge needle 108A (FIGS. 4 and 5) desirably remains inserted in the plantar region of the foot.

Figure 10A:
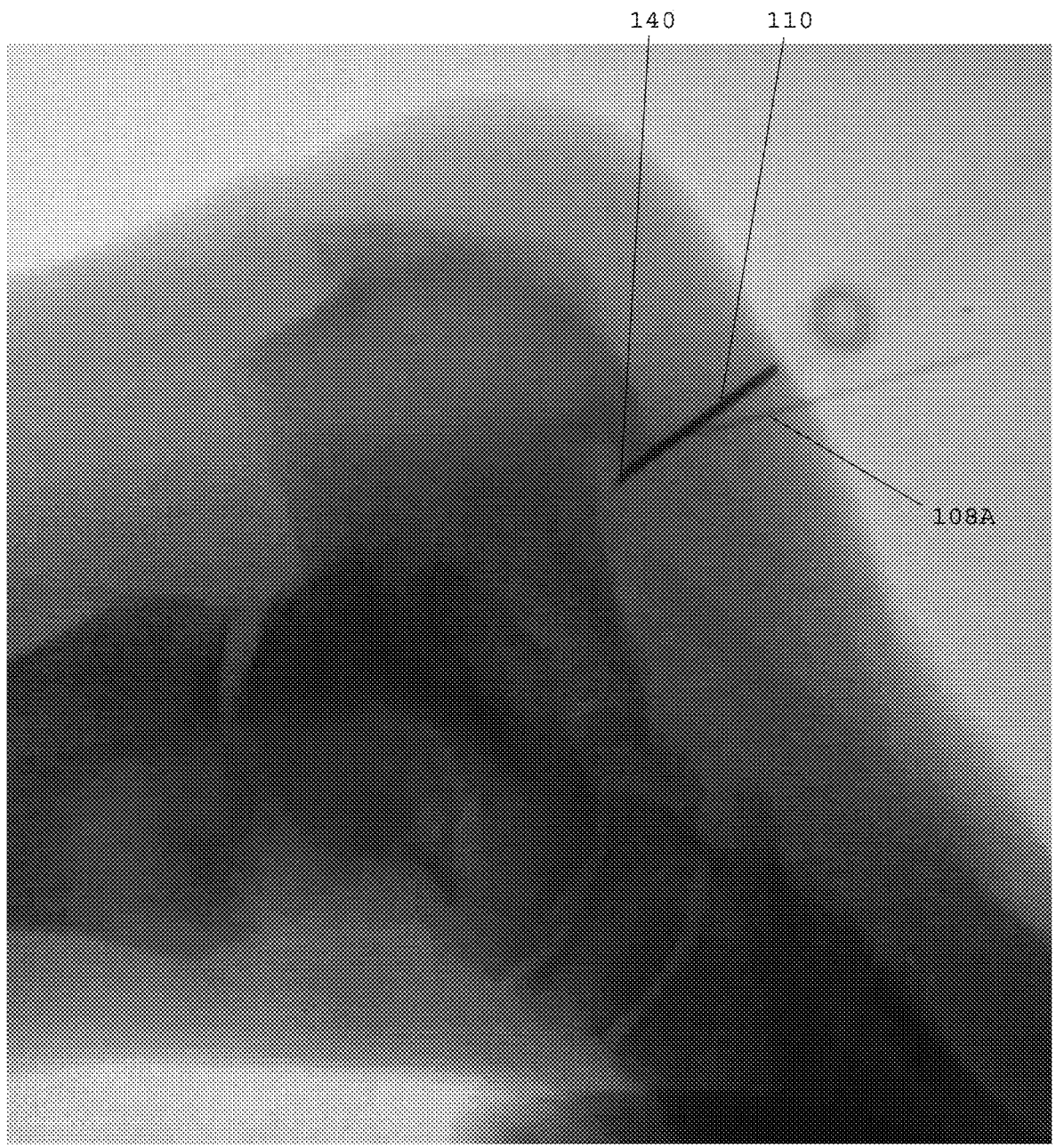
FIG. 10A shows a fluoroscopy view of the patient's foot shown in FIG. 9.
Figure 10B:
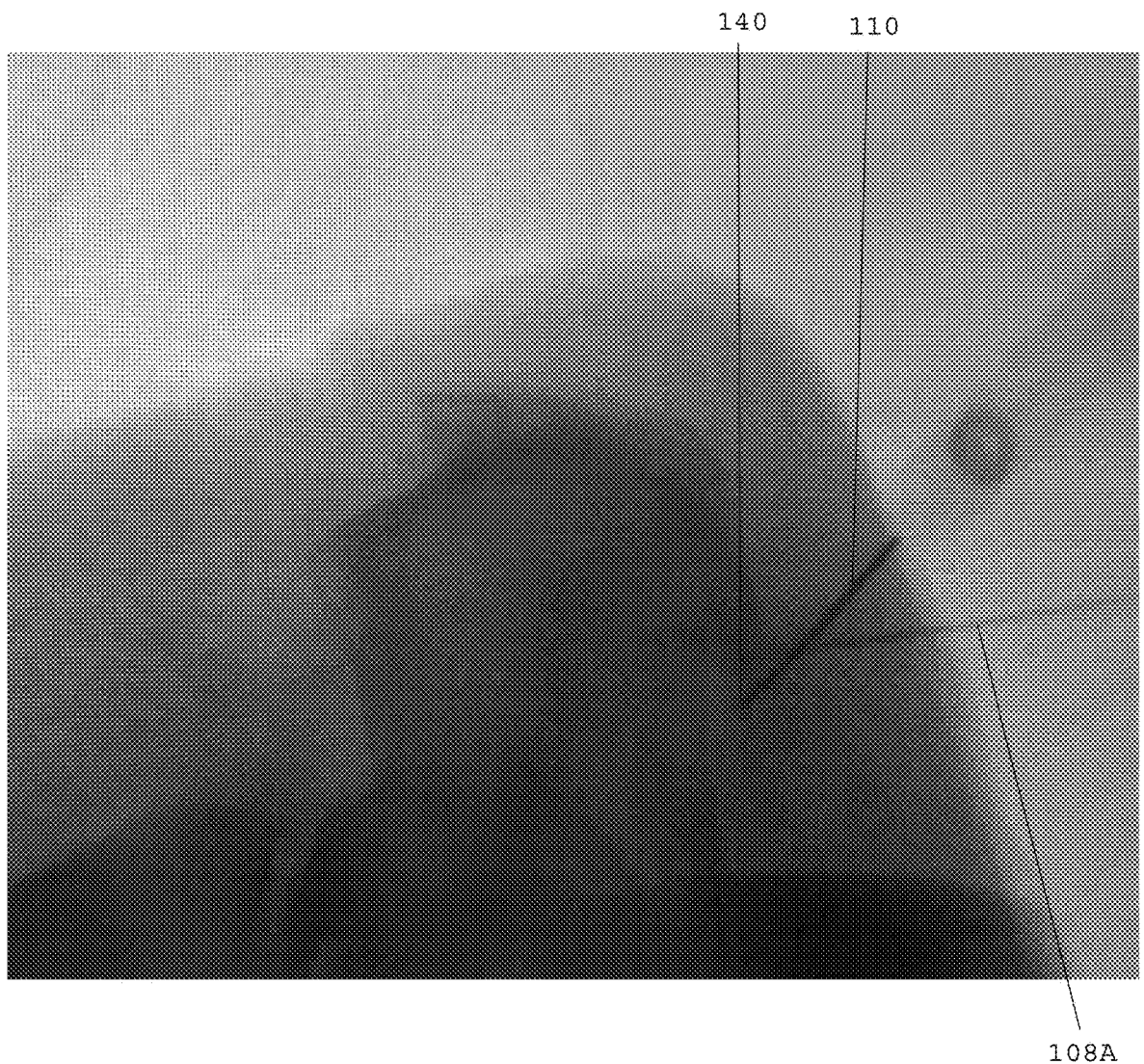
FIG. 10B shows another fluoroscopy view of the patient's foot shown in FIG. 9.
Figure 11A:
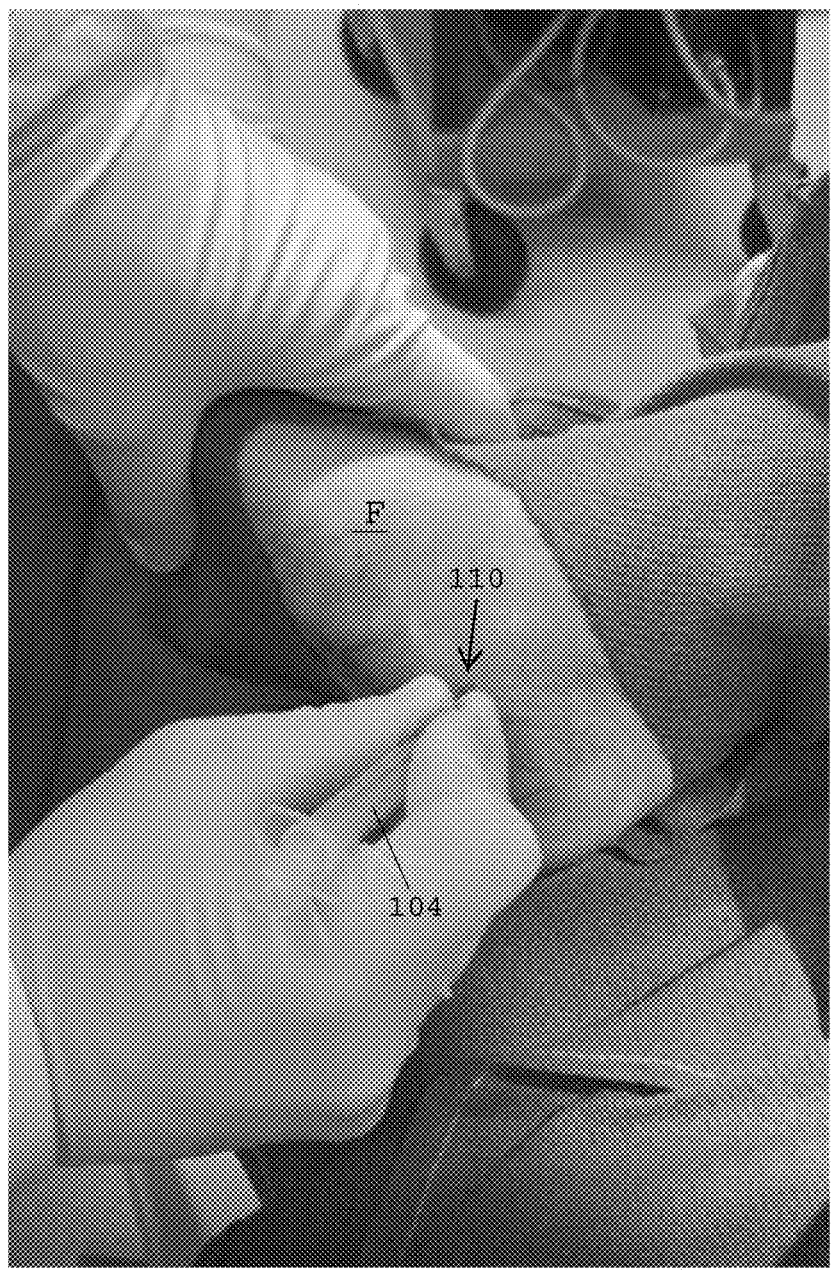
FIG. 11A shows a stage of a method of dissecting a plantar fascia, in accordance with one embodiment of the present patent application.
Figure 11B:
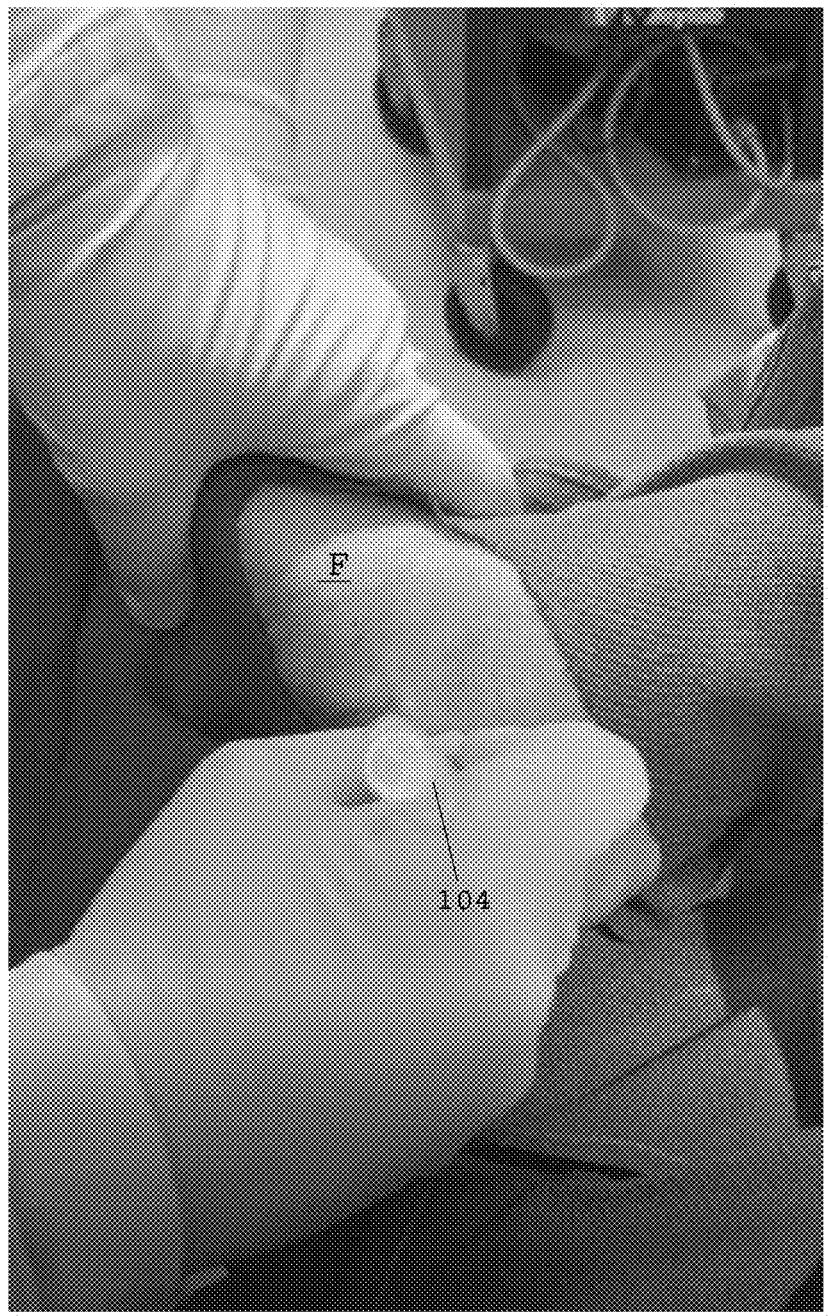
FIG. 11B shows a stage of a method of dissecting a plantar fascia, in accordance with one embodiment of the present patent application.
Figure 11C:
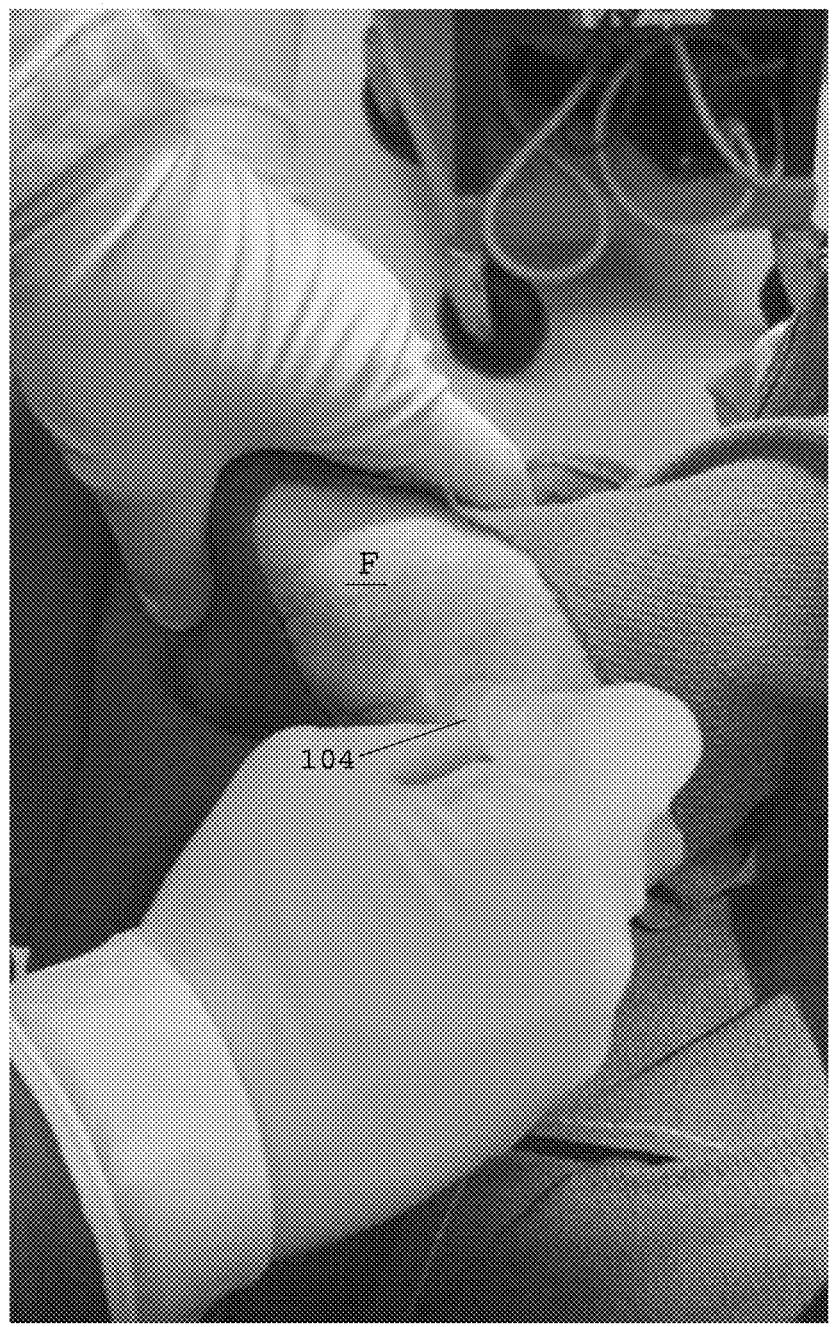
FIG. 11C shows another stage of a method of dissecting a plantar fascia.
Figure 11D:
FIG. 11D shows yet another stage of a method of dissecting a plantar fascia.
Figure 11E:
FIG. 11E shows still another stage of a method of dissecting a plantar fascia.

Referring to FIGS. 10A and 10B, after the 18 gauge needle 110 is inserted, surgical personnel use fluoroscopy to confirm that the sharpened distal tip 140 of the 18 gauge needle 110 is properly inserted, whereby the distal tip is positioned at the location where the plantar fascia originates (i.e., adjacent the heel bone). In one embodiment, surgical personnel may use the fluoroscopic images to reposition the sharpened distal tip of the 18 gauge needle 110 until the sharpened distal tip is properly positioned at the location where the plantar fascia originates. The first 25 gauge needle 108A remains inserted in the plantar region of the foot.

Referring to FIGS. 11A-11E, after the 18 gauge needle 110 (FIG. 9) has been properly inserted into the medial region of the patient's foot F, the surgeon will preferably grasp the base of the syringe 104 for pivoting the sharpened distal tip of the 18 gauge needle back and forth for cutting the patient's plantar fascia. In one embodiment, the 18 gauge needle 110 is preferably swung dorsal to plantar through an arc of about 30-45 degrees. As the distal sharpened tip of the 18 gauge needle is rocked back and forth over the 30-45 degree arc, the sharpened distal tip preferably cuts the medial portion of the plantar fascia.

Figure 12:
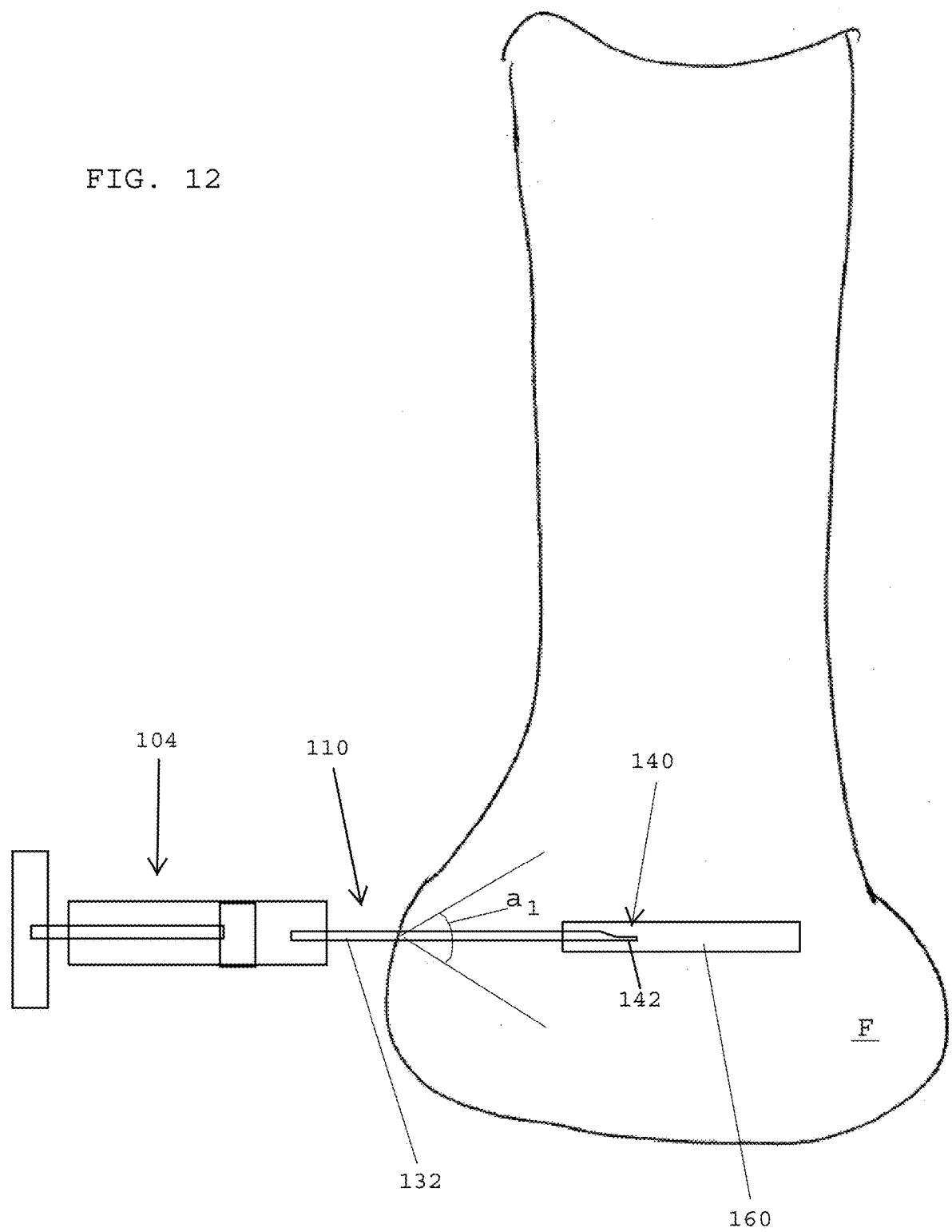
FIG. 12 shows a schematic view of a method of using a sharpened tip of a needle for dissecting a plantar fascia of a foot, in accordance with one embodiment of the present patent application.

FIG. 12 shows a schematic view of the 18 gauge needle 110 being inserted into the medial region of the patient's foot F. The sharpened distal tip 140 having the cutting edges 142 and 144 (FIG. 7B) at the distal end of the elongated shaft 132 of the needle desirably cuts the plantar fascia 160 where it originates adjacent the heel bone. In one embodiment, the surgeon swings the sharpened distal tip 140 back and forth over an arc of movement $\alpha_1$ of about 30-45° for severing the medial portion of the plantar fascia 160 where it originates adjacent the heel bone.

Figure 13A:
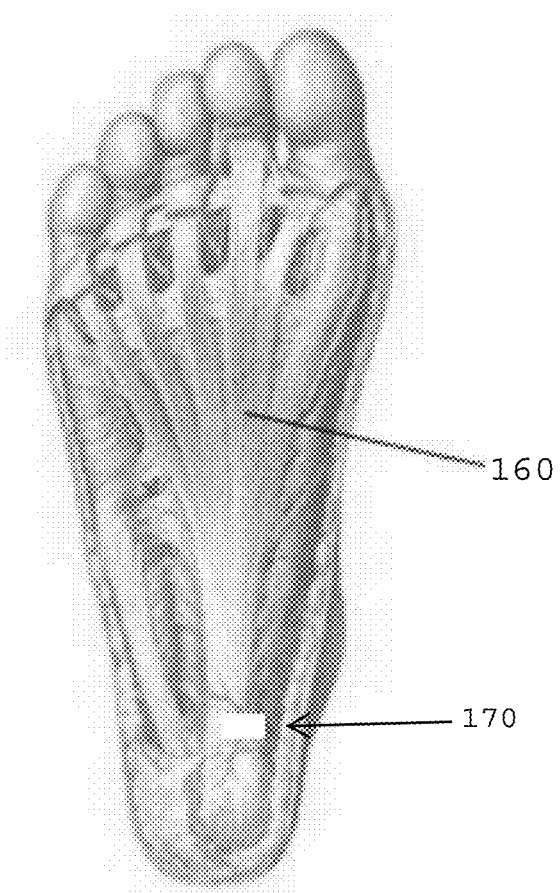
FIG. 13A shows a bottom view of a dissected human foot having a partially cut plantar fascia, in accordance with one embodiment of the present patent application.
Figure 13B:
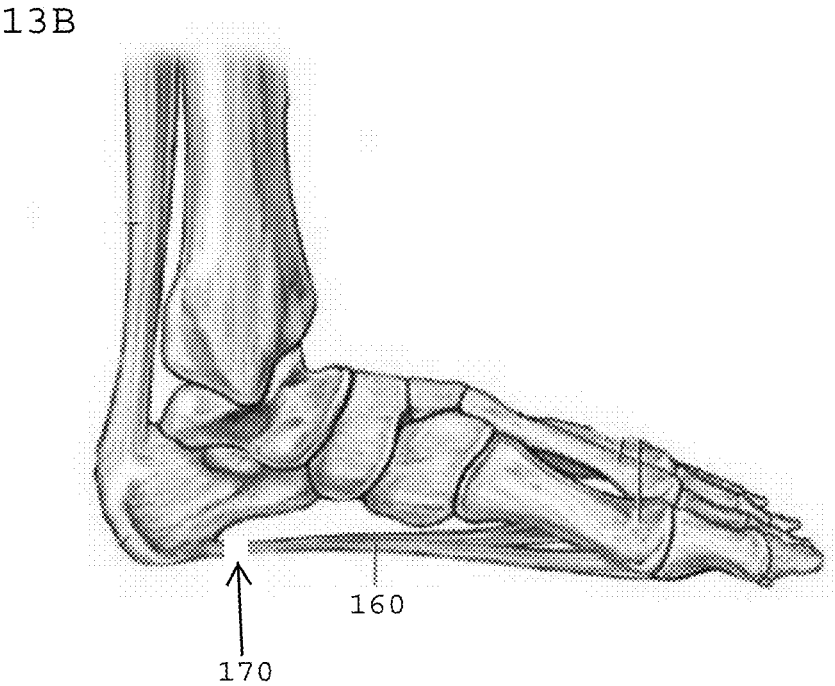
FIG. 13B shows a side view of the human foot shown in FIG. 13A.

FIGS. 13A and 13B show the medial portion of the plantar fascia 160 after it has been cut by the sharpened distal tip of the 18 gauge needle 110 to produce a cut region 170 of the plantar fascia. In one embodiment, the success of the cutting operation may be observed and confirmed using fluoroscopy to determine if additional cutting and/or excising may be necessary. In one embodiment, about ⅔ of the medial part of the center band of the plantar fascia is cut.

Figure 14:
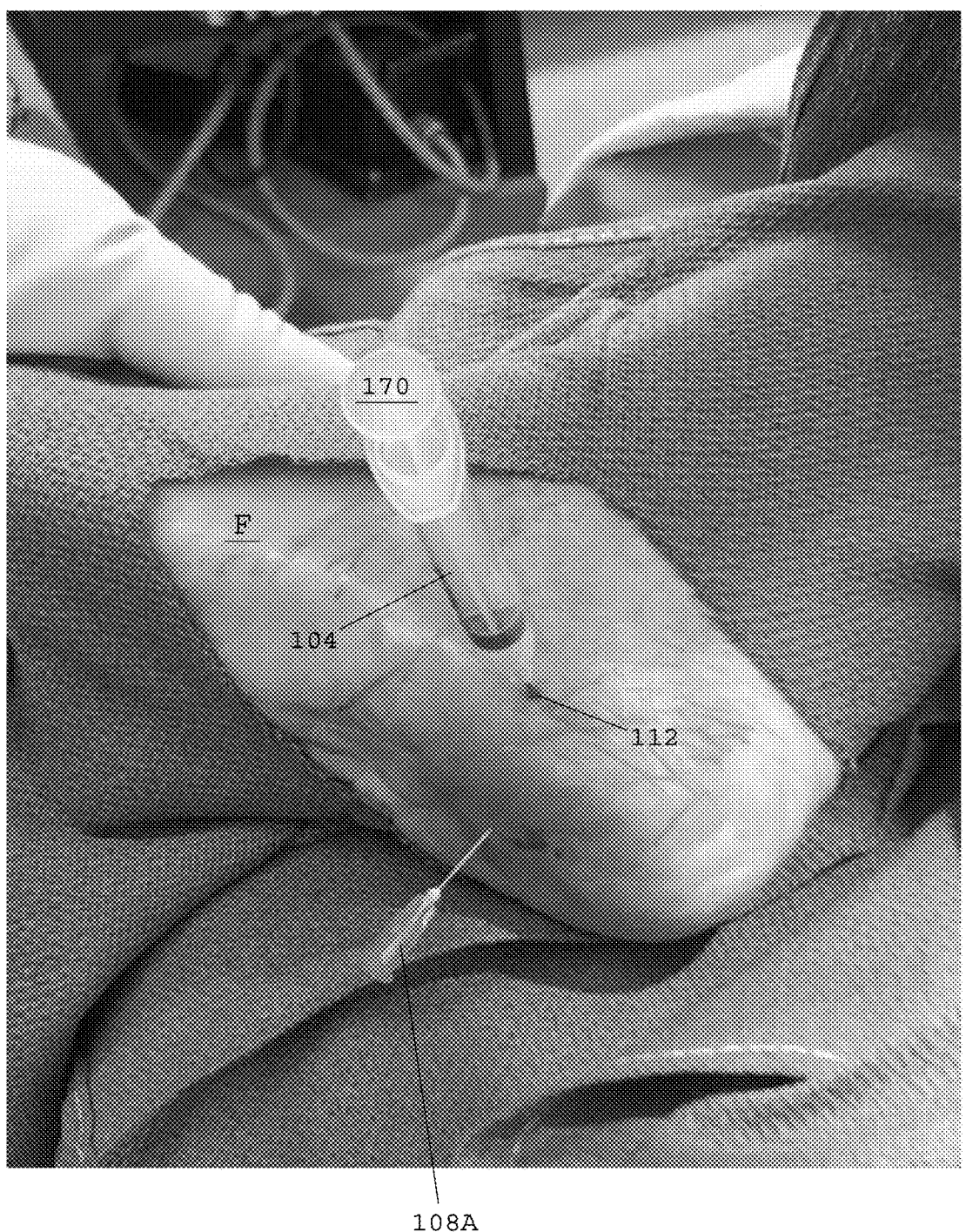
FIG. 14 shows a method of treating plantar fascia including injecting a growth hormone into a location where a plantar fascia has been cut, in accordance with one embodiment of the present patent application.

Referring to FIG. 14, after the plantar fascia has been cut using the sharpened distal tip 140 of the 18 gauge needle 110 (FIG. 12), the 18 gauge needle may be removed from the patient's foot F. In one embodiment, the 22 gauge needle 112 may be inserted into the medial opening previously occupied by the 18 gauge needle 110 (FIG. 12). In one embodiment, prior to inserting the 22 gauge needle 112 into the medial opening, the 22 gauge needle is preferably coupled with the distal end of the syringe 104. The distal tip of the 22 gauge needle 112 is preferably inserted into the container of human growth factor 120 for drawing the human growth factor into the syringe 104.

In one embodiment, after the distal tip of the 22 gauge needle 112 (coupled to the syringe) is inserted into the medial opening previously occupied by the second 25 gauge needle 108B, the plunger 170 of the syringe 104 may be depressed for injecting the human growth factor 120 (FIG. 3) through the 22 gauge needle 112 and into the region of the plantar fascia that has been cut. Fluoroscopy may be used for confirming and directing the positioning of the distal tip of the 22 gauge needle 112. After the human growth factor has been injected, the 22 gauge needle 112 may be removed from the medial region of the foot. In addition, the first 25 gauge needle 108A may be removed from the plantar region of the foot.

Figure 15:
FIG. 15 shows a perspective view of a human foot after a plantar fascia repair procedure has been completed, in accordance with one embodiment of the present patent application.

Referring to FIG. 15, after the 22 gauge needle 112 (FIG. 14) and the first 25 gauge needle 108A (FIG. 14) have been removed from the respective medial and plantar openings, the wounds created by the needles may be covered with adhesive bandages 118.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of treating plantar fasciitis comprising:
    inserting a first needle having a distal tip into a plantar aspect of a foot and advancing the distal tip of said first needle to a location where a plantar fascia originates;
    inserting a second needle having a distal tip into a medial aspect of said foot and advancing the distal tip of said second needle to the location where the plantar fascia originates, wherein the advancing the distal tip of said second needle step forms a medial opening in said foot;
    using medical imaging for confirming that the distal tips of said first and second needles are located where the plantar fascia originates;
    after the using medical imaging step, removing said second needle from said foot, inserting a third needle having a sharpened distal tip into the medial opening in said foot, and advancing the sharpened distal tip of said third needle to the location where the plantar fascia originates;
    using medical imaging for confirming that the sharpened distal tip of said third needle is located where the plantar fascia originates;
    using the sharpened distal tip of said third needle for cutting said plantar fascia;
    after the cutting said plantar fascia step, removing said third needle from said foot, providing a fourth needle coupled with a syringe containing a growth factor, inserting a distal tip of said fourth needle into the medial opening in said foot, and advancing the distal tip of said fourth needle to the location where the plantar fascia originates;
using medical imaging for confirming that the distal tip of said fourth needle is located where the plantar fascia originates;
    engaging said syringe coupled with said fourth needle for injecting said growth factor into said plantar fascia.

2. The method as claimed in claim 1, wherein said third needle has a larger outer diameter than both said second needle and said fourth needle.

3. The method as claimed in claim 2, wherein said first and second needles have an identical outer diameter.

4. The method as claimed in claim 3, wherein said first and second needles are 25 gauge needles, said third needle is an 18 gauge needle, and said fourth needle is a 22 gauge needle.

5. The method as claimed in claim 1, wherein the using medical imaging steps comprise using a fluoroscope.

6. The method as claimed in claim 1, wherein the cutting step comprises moving said sharpened distal tip from a medial direction to a lateral direction across said plantar fascia at the location where the plantar fascia originates.

7. The method as claimed in claim 1, further comprising:
    after injecting said growth factor, removing said first and fourth needles from said foot;
    applying bandages over wounds formed by said first and fourth needles.

8. The method as claimed in claim 1, wherein said third needle comprises:
    a handle; and
    an elongated shaft having a proximal end secured to a distal end of said handle and a distal end including said sharpened distal tip with one or more cutting edges, wherein said sharpened distal tip with said one or more cutting edges defines a distal-most end of said third needle.

9. The method as claimed in claim 8, wherein during the cutting said plantar fascia step; said elongated shaft of said third needle passes through said medial opening in said foot.

10. A method of treating plantar fasciitis comprising:
    inserting a first 25 gauge needle having a distal tip into a plantar aspect of a foot and advancing the distal tip of said first 25 gauge needle to a location where a plantar fascia originates;
    inserting a second 25 gauge needle having a distal tip into a medial aspect of said foot and advancing the distal tip of said second 25 gauge needle to the location where the plantar fascia originates, wherein the advancing the distal tip of said second 25 gauge needle step forms a medial opening in said foot;
    using a fluoroscope for confirming that the distal tips of said first and second 25 gauge needles are located where the plantar fascia originates;
    after the using the fluoroscope step, removing said second 25 gauge needle from said foot, inserting an 18 gauge needle having a sharpened distal tip into the medial opening in said foot, and advancing the sharpened distal tip of said 18 gauge needle to the location where the plantar fascia originates;
    using a fluoroscope for confirming that the sharpened distal tip of said 18 gauge needle is located where the plantar fascia originates;
    using the sharpened distal tip of said 18 gauge needle for cutting said plantar fascia;
    after the cutting said plantar fascia step, removing said 18 gauge needle from said foot, providing a 22 gauge needle coupled with a syringe containing a growth factor, inserting a distal tip of said 22 gauge needle into the medial opening in said foot, and advancing the distal tip of said 22 gauge needle to the location where the plantar fascia originates;
using a fluoroscope for confirming that the distal tip of said 22 gauge needle is located where the plantar fascia originates;
engaging said syringe coupled with said 22 gauge needle for injecting said growth factor into said plantar fascia.

11. The method as claimed in claim 10, wherein the cutting step comprises moving said sharpened distal tip of said 18 gauge needle from a medial direction to a lateral direction across said plantar fascia at the location where the plantar fascia originates.

12. The method as claimed in claim 11, further comprising:
    after injecting said growth factor, removing said first 25 gauge needle and said 22 gauge needle from said foot;
    applying bandages over wounds formed by said first 25 gauge needle and said 22 gauge needle.

13. The method as claimed in claim 10, wherein said 18 gauge needle comprises:
    a handle; and
    an elongated shaft having a proximal end secured to a distal end of said handle and a distal end including said sharpened distal tip with one or more cutting edges, wherein said sharpened distal tip with said one or more cutting edges defines a distal-most end of said 18 gauge needle.

14. The method as claimed in claim 13, wherein during the cutting said plantar fascia step, said elongated shaft of said 18 gauge needle is disposed in said medial opening in said foot.

15. A method of treating foot and heel pain comprising:
inserting a first needle having a distal tip into a plantar aspect of a foot and advancing the distal tip of said first needle to a location where a plantar fascia originates;
inserting a second needle having a distal tip into a medial aspect of said foot and advancing the distal tip of said second needle to the location where the plantar fascia originates, wherein the advancing the distal tip of said second needle step forms a medial opening in said foot;
using fluoroscopy for confirming that the distal tips of said first and second needles are located where the plantar fascia originates;
after the using fluoroscopy step, removing said second needle from said foot, inserting a third needle having a sharpened distal tip into the medial opening in said foot, and advancing the sharpened distal tip of said third needle to the location where the plantar fascia originates;
using fluoroscopy for confirming that the sharpened distal tip of said third needle is located where the plantar fascia originates;
using the sharpened distal tip of said third needle for cutting said plantar fascia;
after the cutting said plantar fascia step, removing said third needle from said foot, providing a fourth needle coupled with a syringe containing a growth factor, inserting a distal tip of said fourth needle into the medial opening in said foot; and advancing the distal tip of said fourth needle to the location where the plantar fascia originates;
using fluoroscopy for confirming that the distal tip of said fourth needle is located where the plantar fascia originates;
engaging said syringe coupled with said fourth needle for injecting said growth factor into said plantar fascia.

16. The method as claimed in claim 15, wherein the sharpened distal tip of said third needle includes at least one cutting edge.

17. The method as claimed in claim 15, further comprising coupling said third needle with a syringe prior to the cutting said plantar fascia step.

18. The method as claimed in claim 15, wherein the cutting said plantar fascia step comprises moving said sharpened distal tip of said third needle from a medial direction to a lateral direction across said plantar fascia at the location where the plantar fascia originates.

19. The method as claimed in claim 18, wherein the cutting said plantar fascia step comprises moving said sharpened distal tip of said third needle in dorsal and plantar directions.

20. The method as claimed in claim 15, wherein said third needle comprises:
a handle; and
an elongated shaft having a proximal end secured to a distal end of said handle and a distal end including said sharpened distal tip with one or more cutting edges, wherein said sharpened distal tip with said one or more cutting edges defines a distal-most end of said third needle, and wherein during the cutting said plantar fascia step, said elongated shaft of said third needle is disposed in said medial opening in said foot.

* * * * *